United States Patent [19]
Hashimoto et al.

[11] Patent Number: 5,820,850
[45] Date of Patent: Oct. 13, 1998

[54] GAS-FILLED AMINO ACID BLOCK CO-POLYMER MICROSPHERES USEFUL AS ULTRASOUND CONTRAST AGENTS

[75] Inventors: Yukio Hashimoto, Washington, D.C.; Rolf Lohrmann, La Jolla, Calif.

[73] Assignee: Molecular Biosystems, Inc., San Diego, Calif.

[21] Appl. No.: 486,770

[22] Filed: Jun. 7, 1995

[51] Int. Cl.$^6$ .................................................. A61K 49/04
[52] U.S. Cl. ............................................................ 424/9.52
[58] Field of Search ........................ 424/9.52, 9.5, 424/9.51; 128/662.02

[56] References Cited

U.S. PATENT DOCUMENTS

| | | | |
|---|---|---|---|
| 4,572,203 | 2/1986 | Feinstein . | |
| 4,844,882 | 7/1989 | Widder et al. . | |
| 4,957,656 | 9/1990 | Cerny et al. . | |
| 5,137,928 | 8/1992 | Erbel et al. . | |
| 5,149,543 | 9/1992 | Cohen et al. . | |
| 5,190,982 | 3/1993 | Erbel et al. . | |
| 5,505,932 | 4/1996 | Grinstaff et al. | 424/9.3 |
| 5,540,909 | 7/1996 | Schutt | 424/9.52 |
| 5,567,415 | 10/1996 | Porter | 424/9.52 |

FOREIGN PATENT DOCUMENTS

| | | |
|---|---|---|
| 0458745 | 11/1991 | European Pat. Off. . |
| 0554213 | 8/1993 | European Pat. Off. . |
| 0554213 B1 | 8/1993 | European Pat. Off. . |
| 19510690 | 9/1996 | Germany . |
| WO 89/06978 | 8/1989 | WIPO . |
| WO 91/09629 | 7/1991 | WIPO . |
| WO 92/05806 | 4/1992 | WIPO . |
| WO 92/17212 | 10/1992 | WIPO . |
| WO 92/17213 | 10/1992 | WIPO . |
| WO 92/18164 | 10/1992 | WIPO . |
| WO 93/02712 | 2/1993 | WIPO . |
| WO 95/06518 | 3/1995 | WIPO . |
| WO 96/04018 | 2/1996 | WIPO . |
| WO 96/15815 | 5/1996 | WIPO . |

OTHER PUBLICATIONS

Ophir et al., "Contrast Agents in Diagnostic Ultrasound." *Ultrasound in Med. & Biol.* 15(4):319–333 (1989).

de Jong et al., "Quantification of Transpulmonary Echocontrast Effects." *Ultrasound in Med. & Biol.* 19(4):279–288 (1993).

Schneider et al., "Polymeric Microballoons as Ultrasound Contrast Agents. Physical and Ultrasonic Properties Compared with Sonicated Albumin." *Inv. Radiol.* 27:134–139 (1992).

de Jong et al., "Absorption and Scatter of Encapsulated Gas Filled Microspheres: Theoretical Considerations and Some Measurements." *Ultrasonics* 30(2):95–103 (1992).

Wen et al., "Thermodynamics of Some Perfluorocarbon Gases in Water." *J. Sol. Chem.* 8(3):225–240 (1979).

*Primary Examiner*—Gary E. Hollinden
*Assistant Examiner*—Michael G. Hartley
*Attorney, Agent, or Firm*—Morrison & Foerster

[57] ABSTRACT

The present invention relates to gas-filled microspheres useful as ultrasound contrast agents. More particularly, the present invention relates to gas-filled microspheres prepared from amphiphilic poly amino acid block co-polymers and a pharmacologically acceptable water-insoluble gas. The hydrophobic block of the co-polymer is formed from amino acids possessing hydrophobic side-chains, for example, leucine, isoleucine, valine, and phenylalanine, and the hydrophilic block of the co-polymer is formed from amino acids possessing hydrophilic side-chains, for example, glutamic acid (and its ionized form, glutamate), aspartic acid (and its ionized form, aspartate), and lysine.

16 Claims, 5 Drawing Sheets

GAS-FILLED AMINO ACID BLOCK CO-POLYMER MICROSPHERES USEFUL AS ULTRASOUND CONTRAST AGENTS

TECHNICAL FIELD

The present invention relates to gas-filled microspheres useful as ultrasound contrast agents. More particularly, the present invention relates to gas-filled microspheres prepared from amphiphilic poly amino acid block co-polymers.

BACKGROUND

Diagnostic ultrasonic imaging is based on the principle that waves of sound energy can be focused upon an area of interest and reflected in such a way as to produce an image thereof. The ultrasonic scanner utilized is placed on a body surface overlying the area to be imaged, and sound waves are directed toward that area. The scanner detects reflected sound waves and translates the data into video images. When ultrasonic energy is transmitted through a substance, the amount of energy reflected depends upon the velocity of the transmission and the acoustic properties of the substance. Changes in the substance's acoustic properties (e.g., variations in acoustic impedance) are most prominent at the interfaces of different acoustic densities, such as liquid-solid or liquid-gas. Consequently, when ultrasonic energy is directed through tissue, organ structures generate sound reflection signals for detection by the ultrasonic scanner. These signals can be intensified by the proper use of a contrast agent.

Ultrasound imaging agents of particular importance employ the use of gas because of its efficiency as a reflector of ultrasound. Resonant gas bubbles scatter sound a thousand times more efficiently than a solid particle of the same size. Ophir and Parker (*Ultrasound in Medicine and Biology*, 1989, Vol. 15, No. 4, pp. 319–333), describe various types of gas-containing ultrasonic contrast agents. One major class of gas-containing ultrasound contrast agents described by Ophir and Parker are the encapsulated gas microbubbles or microspheres. The gas bubble is surrounded by a shell composed of a protein or other biocompatible material. A current commercial microsphere contrast agent is ALBUNEX® (Molecular Biosystems, Inc., San Diego, Calif.) which is composed of human serum albumin encapsulated air microspheres and has a suitable shelf-life. See, for example, U.S. Pat. Nos. 4,572,203 and 4,844,882. The creation of such a protein shell around the bubble prevents coalescence and permits storage of the microspheres (1–10 micron diameter) for 20 weeks or more without loss.

Encapsulated microbubbles also offer a solution to the problem of size: microspheres are superior in that they can be manufactured to be predominantly less than 8 microns in diameter, as required to pass through the pulmonary capillaries (dejong, N. et al., *Ultrasound Med. Biol.* 19:279–288, 1993).

Recent teachings have centered on improving the properties of the microsphere shell, primarily to enhance the in vivo stability. For example, Giddey (PCT/EP91/01706) has proposed pre-emulsifying air in a protein solution containing a large percentage of a viscosifying agent (40%–80% polyols) and subject it to mechanical shear in a high speed blender. Bubbles of the appropriate size are collected and coated with a suitable surfactant to stabilize them in a soft shell. Holmes (PCT WO 92/17213) proposed to enhance the in vivo stability of protein microspheres by strengthening the shell with biodegradable chemical crosslinking reagents. Bichon et al. (EPA 90/810367) and Schneider et al. (*Inv. Radiol.* 27:134–139, 1992) describe the production of porous (5 to 2000 nm pore size) polymeric "microballoons", the porous envelope of the which offers improved resiliency. Erbel and Zotz (U.S. Pat. No. 5,190,982) describe a cross-linked polymeric microcapsule in which air is entrapped.

Studies have shown that the presence of a rigid shell dampens resonance energy of the bubble and decreases backscatter (deJong, N. et al., *Ultrasonics* 30:95–103, 1992). Also, the bubble resonance frequency is shifted to shorter wavelengths (Schneider, M. et al., *Invest. Radiol.* 27:134–139, 1991). This shift can be a problem in clinical applications because penetration of the ultrasound pulse from the acoustic scanner is a direct function of the frequency; shorter wavelengths, e.g., 7.5 to 12.5 MHz, do not penetrate tissue well. Typical frequencies for diagnostic ultrasound are 2–7.5 MHz.

The inventors have discovered that a poly amino acid block co-polymer with a hydrophilic end and a hydrophobic end may be used to generate a stable membrane for a gas-filled microsphere. Due to its amphiphilic properties, these block co-polymers form micelles when placed in solution. In the presence of a pharmacologically acceptable water-insoluble gas, for example, a perfluorocarbon gas, such a solution can form gas-filled microspheres by acoustic or mechanical cavitation techniques. The polymer membrane forms by interaction between the hydrophobic polymer side chains and the hydrophobic gas. The membrane shell is then further stabilized by the formation of a polymer complex network, due to polyamide hydrogen bonding. The gas-filled microspheres may be encouraged to remain dispersed in the aqueous medium by the presence of negatively or positively charged functional groups in the hydrophilic portion of the block co-polymer.

SUMMARY OF THE INVENTION

One aspect of the present invention pertains to compositions suitable for use as ultrasonic imaging agents, which compositions comprise a suspension of gas-filled microspheres, said microspheres comprising:

(a) an outer membrane comprising an amphiphilic amino acid block co-polymer, said co-polymer having a hydrophobic polymer block comprised of hydrophobic amino acids, and a hydrophilic polymer block comprised of hydrophilic amino acids; said outer membrane encapsulating (b) a pharmacologically acceptable water-insoluble gas.

Preferably, said hydrophobic amino acids are alpha-amino acids. More preferably, said hydrophobic amino acids are alpha-amino acids selected from the group consisting of leucine, isoleucine, valine, and phenylalanine. In one preferred embodiment, said hydrophobic amino acids are leucine.

Preferably, said hydrophilic amino acids are alpha-amino acids. More preferably, said hydrophilic amino acids are alpha-amino acids selected from the group consisting of glutamic acid, glutamate, aspartic acid, aspartate, and lysine. In one preferred embodiment, said hydrophilic amino acids are glutamate.

Preferably, said water-insoluble gas is a perfluoroalkane having 1 to 5 carbon atoms, more preferably 3 to 5 carbon atoms. In one preferred embodiment, said water-insoluble gas is perfluoropropane.

In a preferred embodiment, said hydrophobic amino acids are leucine; said hydrophilic amino acids are glutamate; and said water-insoluble gas is perfluoropropane.

Another aspect of the present invention is a method of enhancing the contrast of tissues and/or organs of a patient in an ultrasonic image thereof, comprising the steps:

(a) injecting the microsphere composition described above into the patient;

(b) applying ultrasonic energy to said tissue and/or organs;

(c) detecting ultrasonic energy that is reflected from the tissues and/or organs; and (d) translating the reflected energy into an image.

DETAILED DESCRIPTION

Figure 1:
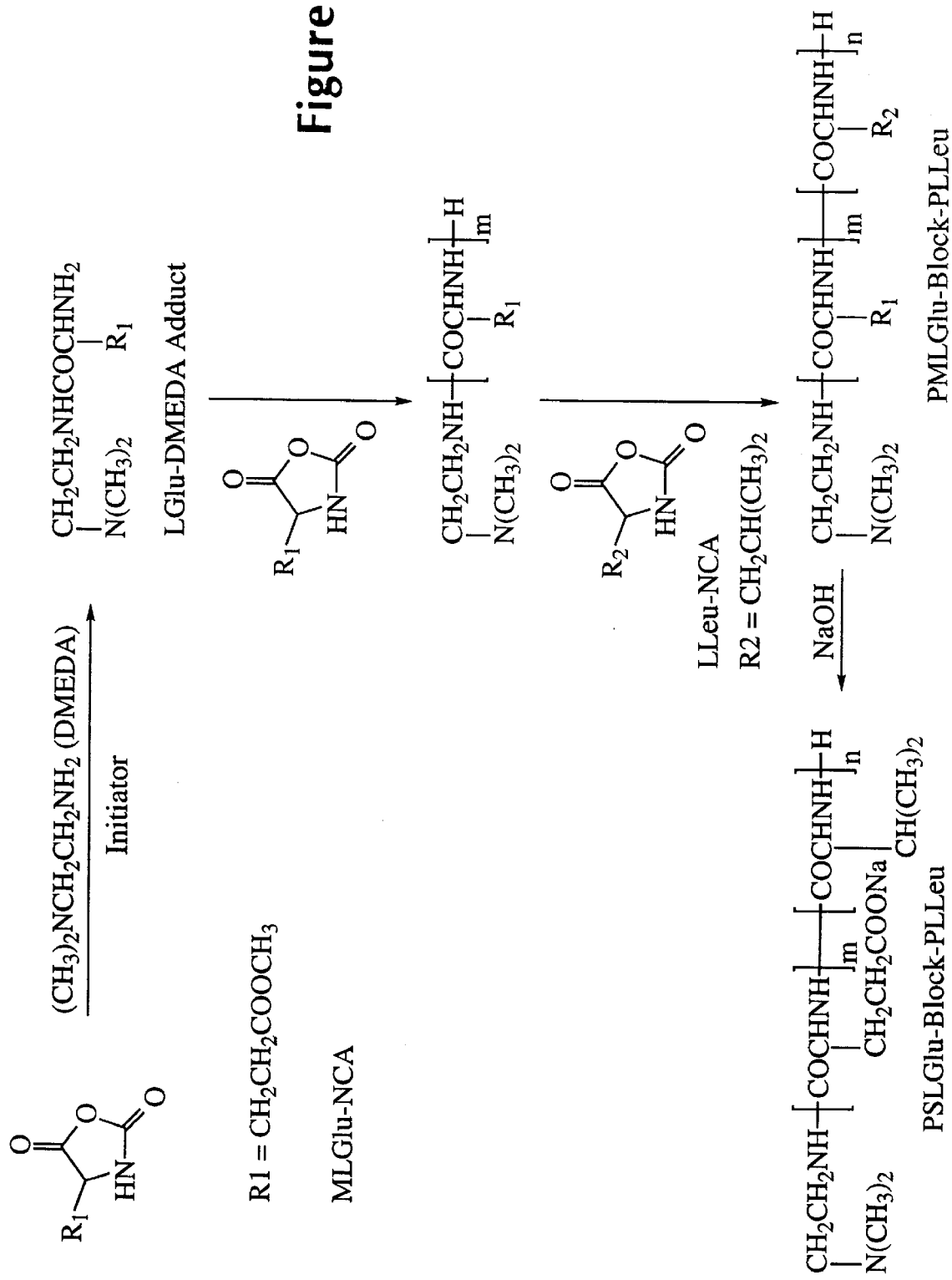
FIG. 1 is a flow chart that illustrates a synthetic route for the preparation of the block co-polymer PSLGlu-block-PLLeu.

The present invention therefore provides for the preparation of gas-filled microspheres suitable for use as ultrasound contrast agents. These microspheres are prepared from amphiphilic amino acid block co-polymers (i.e., block co-polymers which possess a hydrophobic block and a hydrophilic block) and a pharmacologically acceptable water-insoluble gas.

The term "amino acid" is used herein in the conventional sense to refer to organic chemical moieties which comprise an amino group ($—NH_2$) and a carboxylic acid group ($—COOH$). One important class of amino acids are the so-called alpha-amino acids, wherein the amino group is attached to the alpha-carbon, that is, to the carbon atom adjacent to the carboxylic acid carbon.

Alpha-amino acids may conveniently be represented by the formula $H_2N—CH(R)—COOH$, wherein the group $—R$ is conventionally referred to as the "side-chain". Side-chains may vary in size, shape, charge and chemical reactivity. A large number of alpha-amino acids are known, including for example, the twenty common and well-known naturally occurring alpha-amino acids.

Side-chains may be hydrophobic or hydrophilic. The terms "hydrophobic" and "hydrophilic" are used herein in the conventional sense to refer to chemical moieties which, respectively, lack affinity and possess affinity, for water. Examples of hydrophobic side chains include, for example, $—CH_2CH(CH_3)_2$ (yielding leucine), $—CH(CH_2CH_3)CH_3$ (yielding isoleucine), $—CH(CH_3)_2$ (yielding valine), and $—CH_2—C_6H_5$ (yielding phenylalanine). Examples of hydrophilic side chains include, for example, $—CH_2—COOH$ (yielding aspartic acid, or in ionized form, aspartate), $—CH_2CH_2—COOH$ (yielding glutamic acid, or in ionized form, glutamate), and $—(CH_2)_4—NH_2$ (yielding lysine). These examples are shown in the following table.

| Nature | Side Chain | Name | One-Letter | Three-Letter |
|---|---|---|---|---|
| hydrophobic | $—CH_2CH(CH_3)_2$ | leucine | L | H—Leu—OH |
| hydrophobic | $—CH(CH_2CH_3)CH_3$ | isoleucine | I | H—Ile—OH |
| hydrophobic | $—CH(CH_3)_2$ | valine | V | H—Val—OH |
| hydrophobic | $—CH_2—C_6H_5$ | phenylalanine | F | H—Phe—OH |
| hydrophilic | $—CH_2—COOH$ | aspartic acid | D | H—Asp—OH |
| hydrophilic | $—CH_2—COO$ | aspartate | D | H—Asp—O |
| hydrophilic | $—CH_2CH_2—COOH$ | glutamic acid | E | H—Glu—OH |
| hydrophilic | $—CH_2CH_2—COO$ | glutamate | E | H—Glu—O |
| hydrophilic | $—(CH_2)_4—NH_2$ | lysine | K | H—Lys—OH |

If the side-chain group, R, is not $—H$, the central (alpha) carbon will be chiral, and the alpha-amino acid will be optically active. Thus, optically active alpha-amino acids may produce a polymer in any of its enantiomeric, diastereomeric, or stereoisomeric forms. For example, glycine, for which R is $—H$, is not optically active, whereas alanine, for which R is $—CH_3$, is optically active and may be in D- or L-forms, denoted D-alanine or L-alanine, respectively.

The alpha amino functional group ($—NH_2$) of one alpha amino acid may react with an acid functional group ($—COOH$) attached to the alpha-carbon of another alpha amino acid to form an amide (or peptide) linkage ($—NHCO—$) therebetween. If this process is repeated, an amino acid polymer, also referred to as a poly amino acid (or polypeptide) may be formed, comprising a plurality of alpha amino acids linked by amide (or peptide) linkages.

The term "polymer" is used herein in the conventional sense to refer to molecules which may be described as consisting of a plurality of repeating monomer units which may be the same or different. The term "poly amino acids", as used herein, relates to polymers formed from amino acids, wherein the amino acids may be the same or different.

Polymers wherein all the monomer units are identical are often referred to as homopolymers, whereas polymers wherein all the monomer units are not identical are often referred to as co-polymers (also commonly known as mixed polymers, or heteropolymers). For example a co-polymer consisting of monomeric units A and B may be referred to as an A-B co-polymer.

Co-polymers may conveniently be described by their structure. For A-B co-polymers wherein the A and B monomer units are randomly ordered, the co-polymer may be referred to as an (e.g., . . . A-A-B-A-B-B-A . . . ). For A-B co-polymers wherein every A monomer is situated between two B monomers, (i.e., . . . B-A-B-A-B-A-B . . . ), the co-polymer may be referred to as an A-B alternating co-polymer. For A-B co-polymers wherein monomers A and B never appear in isolation, but instead in blocks of 2 or more of the same monomer, the co-polymer may be referred to as an A-B block co-polymer (e.g., A-A-A-A-B-B-B).

A distinguishing characteristic of co-polymers is the relative number of different monomer units; for example, a co-polymer consisting of twenty A monomer units and thirty B monomer units (e.g., $(AABBB)_n$) may be said to have a monomer ratio of A:B of 0.67 (i.e., 20/30).

Poly amino acids may be linear, branched, or cyclic. For example, two free ends of a linear or branched poly amino acid (i.e., a $—NH_2$ end and a $—COOH$ end) may be linked to form a cyclic structure. Also, alpha-amino acids with more than two reactive functional groups, such as lysine which possesses two reactive $—NH_2$ groups (of differing reactivity, as well as a —COOH group) and aspartic acid which possesses two —COOH groups (of differing reactivity, as well as an —NH$_2$ group), may permit branching and/or cyclization of a polymer formed therefrom.

One class of linear poly amino acids may be represented by the formulae:

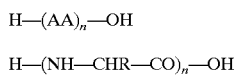

wherein n is positive integer, AA represents an alpha amino acid, and R is an alpha-amino acid side chain attached to the alpha-carbon of an alpha amino acid, and the n amino acids (AA) and n side-chains (R) are independently the same or different. When all the n R groups are the same, the poly amino acid is a homopolymer. When all n R groups are not the same, the polymer may be referred to as a co-polymer. (Note that implicit within these formulae is the optional presence of an end-group, which may arise during polymerization; for example, the terminal —COOH group may be derivatized to include a portion of the polymerization initiator, for example, as an amide, for example, as —CONH—CH$_2$CH$_2$—N(CH$_3$)$_2$, as described below.)

One class of amphiphilic poly amino acid polymers which are useful in the present invention may conveniently be described as A-B block co-polymers, and comprise a first hydrophilic polymer block (formed using hydrophilic alpha-amino acids, AA$^1$, as monomer units) and a second hydrophobic polymer block (formed using hydrophobic alpha-amino acids, AA$^2$, as monomer units), and may be represented by the following formulae:

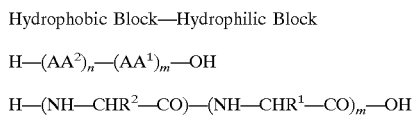

wherein n and m are positive integers from 1 to about 100, more preferably from about 20 to about 50; AA$^1$ are hydrophilic amino acids which are independently the same or different; AA$^2$ are hydrophobic amino acids which are independently the same or different; R$^1$ are hydrophilic amino acid side chains which are independently the same or different; and R$^2$ are hydrophobic amino acid side chains which are independently the same or different. Preferably, all AA$^1$ are the same, all AA$^2$ are the same, all R$^1$ are same, and all R$^2$ are the same. (Note again that implicit within these formulae is the optional presence of an initiator end-group, which may arise during polymerization.)

The first block may be described as a "hydrophobic block", and is a poly amino acid wherein the amino acids are characterized as having hydrophobic amino acid side-chains. Examples of hydrophobic side-chains include the hydrocarbyls of 2 to about 20 carbons atoms, more preferably 3 to about 10 carbons, including, for example, —CH(CH$_3$)$_2$, —CH$_2$CH(CH$_3$)$_2$, —CH(CH$_2$CH$_3$)CH$_3$, and —CH$_2$C$_6$H$_5$. Examples of hydrophobic amino acids include valine, leucine, isoleucine, and phenylalanine.

The second block may be described as a "hydrophilic block", and is a poly amino acid wherein the amino acids are characterized as having hydrophilic amino acid side-chains. Hydrophilic side-chains often comprise hydrophilic functional groups, such as amino (i.e., —NH$_2$ or —NH$_3^+$) groups or carboxylic acid groups (i.e., —COOH or —COO$^-$). Examples of such amino acids include lysine, glutamic acid (and its ionized form, glutamate), and aspartic acid (and its ionized form, aspartate).

For example, one poly amino acid which is useful in the present invention is the block co-polymer formed from L-leucine (i.e., with hydrophobic side-chain —CH$_2$CH(CH$_3$)$_2$) and sodium-L-glutamate (i.e., with hydrophilic side-chain —CH$_2$CH$_2$COONa), which may be represented as PLLeu-block-PSLGlu. Similarly, the block co-polymer formed from L-leucine and gamma-methyl-L-glutamate (i.e., with potentially hydrophilic side-chain —CH$_2$CH$_2$COOCH$_3$) may be represented as PLLeu-block-PMLGlu).

Although simple amino acids may be reacted directly to form poly amino acids, it is often synthetically preferable to form the polymer using derivatized amino acids, so as to more carefully control the reaction, and thereby provide inter alia, (i) control of which functional groups react to form covalent linkages; (ii) control the rate and degree of reaction; and (iii) improved yields of the desired polymer.

A wide variety of synthetic methods for forming poly amino acids, as well as amino acid co-polymers, are well known in the art (H. Leuchs (1906) *Ber. dtsch. Chem. Ges* 39:857; Bamford et al. (1956) SYNTHETIC POLYPEPTIDES (Academic Press, New York); E. Katchalski and M. Sela (1958) *Adv. Protein. Chem.* 13:243–492). For example, an alpha-amino acid or a derivative thereof may be converted by reaction with phosgene (i.e., COCl$_2$) in tetrahydrofuran (THF) to the cyclic amino acid N-carboxy anhydride (i.e., "AA-NCA"; see for example, FIG. 1). For amino acids possessing functional groups other than alpha-carboxy and alpha-amino, suitable protecting strategies are preferably employed. For example, the beta-carboxy and gamma-carboxy groups of aspartic and glutamic acid, respectively, may be protected, for example, as the methyl ester (i.e., beta-methyl-aspartate and gamma-methyl-glutamate, respectively), and the epsilon-amino group of lysine may be protected, for example, as a benzylcarboxy amide.

A first amino acid N-carboxy anhydride (i.e., AA$^1$-NCA) may then be reacted with an "initiator". Suitable initiators for amino acid polymerization reactions are aprotic bases, for example, tertiary amines, which act to deprotonate the amino acid NCA group before it can polymerize. For certain bases, such as primary amines, the base will react with the amino acid NCA group to form a monomer-initiator adduct. An example of a suitable initiator is N,N-dimethylethylenediamine (i.e., N,N-DMEDA, (CH$_3$)$_2$N—CH$_2$CH$_2$—NH$_2$), which reacts with AA$^1$-NCA to give an amino acid-initiator adduct (i.e., AA$^1$-DMEDA) with the release of carbon dioxide (i.e., CO$_2$). The resulting AA$^1$-DMEDA adduct will react again with another AA$^1$-NCA molecule to give the dimer adduct, (AA$^1$)$_2$-DMEDA. This reaction will repeat itself under anhydrous conditions until all the AA$^1$-NCA is consumed, to give (AA$^1$)$_n$-DMEDA. Once the reaction is complete, a second amino acid N-carboxy anhydride (i.e., AA$^2$-NCA), may be added and the reaction continued to yield the desired block co-polymer, (AA$^2$)$_m$(AA$^1$)$_n$-DMEDA.

One distinguishing feature of a polymer is the number of monomer units it comprises. Mixtures of polymers of varying lengths may be characterized by an "average degree of polymerization", DPn. For many polymer syntheses, the DPn may be approximated using various experimental parameters. For example, for polymerization reactions in which the initiator is incorporated into the growing polymer, as is the case for primary amine initiators in the above example, the number of polymer molecules may be approximated by the number of initiator molecules (see *Kobunshi*

Kagaku vol. 30, 338, 365–375 (1973) Japanese). The average length of the polymer molecules may then be controlled and approximated by the total number of monomer units available (or alternatively, the concentration of monomer, [AA]) divided by the number of initiator molecules (or alternatively, the concentration of initiator, [Initiator]); that is, $DPn \approx [AA]/[Initiator]$. For a block co-polymerization using two monomers, one may approximate the DPn as $([AA^1]+[AA^2])/[Initiator]$. In the example described above, therefore, one may approximate the DPn as $([AA^1\text{-NCA}]+[AA^2\text{-NCA}])/[N,N\text{-DMEDA}]$. For polymerization reactions in which the initiator is not incorporated into the growing polymer (as is often observed, for example, when secondary and tertiary amines or other bases are employed), the actual DPn is higher than that predicted by the above calculation.

Due to their amphiphilic properties, these block co-polymers form micelles when placed in solution. Upon cavitation in the presence of a water-insoluble gas, gas-filled microspheres may be formed. Any of a variety of conventional and well-known cavitation methods may be employed, including, for example, ultrasound sonication (using, for example, a high frequency sonication horn) and mechanical cavitation (using, for example, a colloid milling apparatus). Such techniques are exemplified in, inter alia, U.S. Pat. Nos. 4,957,656; 5,137,928; 5,190,982; 5,149,543; international patent publications WO 92/17212; WO 92/18164; WO 91/09629; WO 89/06978; WO 92/17213; and WO 93/02712; and European patent publications 458,745A, 458,745A1 and 554,213A1.

For example, ultrasound cavitation may be performed by submersing a high frequency (i.e., about 5–50 kilohertz) horn in an aqueous solution of the block co-polymer, in the presence of a water-insoluble gas (which may be introduced, for example, by bubbling). For such apparati, horn frequency, power output, and duration of sonication, as well as the gas-to-liquid ratio are the principal process parameters which affect the characteristics (mean size, size distribution, and concentration of microspheres) of the product. The appropriate gas-to-liquid ratio will depend on, inter alia, the geometry of the apparatus and the physical characteristics of the gas (solubility, density, molecular weight, etc.). These parameters may be adjusted empirically to provide a microsphere product having the desired characteristics.

Alternatively, mechanical shearing and hydrodynamic cavitation may be performed using apparati such as high speed mixers, mills, fluidizers and the like. A preferred apparatus is a colloid mill which may be defined as a machine consisting of a high-speed rotor and a stator, wherein dispersion or emulsification is effected by the opposing faces. For such apparati, rotor speed, gap size and gas-to-liquid ratio are the principal process parameters which affect the characteristics of the product. Again, these parameters may be adjusted empirically to provide the desired product.

Due to their surface activity, many amphiphilic block copolymers will form microbubbles upon cavitation in the presence of a water-insoluble gas. However, the microbubbles may disappear after a period of time. An important feature of this invention is that the hydrophobic block copolymer forms a polymer complex network on the surface of the micro gas bubble. The network is stabilized not only by hydrophobic interactions but also by hydrogen bonding within the beta-sheet structure of the hydrophobic polyamino acid block. These hydrogen bonds restrict Brownian movement of the block copolymer on the surface of the microbubble. In order to form microspheres that are stable in shape and size, a fine balance between hydrophobic and hydrophilic forces is required. This can be accomplished by adjusting various parameters such as the number of and type of amino acids present in the block copolymer and is approximately expressed by the hydrophilicity and the average degree of polymerization.

The hydrophobic/hydrophilic character of the block co-polymer may be approximated by its hydrophilicity. As used herein, the term "hydrophilicity" refers to the ratio of the number of hydrophilic amino acids to the total number of amino acids in the block co-polymer. For example, in the block co-polymer $(AA^1)_{10}(AA^2)_{20}$, the hydrophilicity is calculated to be $20/(10+20)=0.66$.

For given hydrophobic and hydrophilic amino acids, a wide range of block co-polymers may be formed; for example, one may prepare small or large co-polymers, with independently small or large hydrophobic and hydrophilic blocks. Not all of these various co-polymers will, upon cavitation, yield microspheres. For example, the co-polymer may be surface active, and yield microspheres; or it may be surface active, but yield only a foam; or it may be non-surface active, and yield an opaque solution; or it may precipitate. By preparing a range of co-polymers with differing hydrophilicities and average degrees of polymerization, one may easily prepare a "phase diagram". For example, a suitable phase diagram may be prepared with the calculated average degree of polymerization along the horizontal axis and the calculated hydrophilicity along the vertical axis. By plotting data-points for a range of block co-polymers, the boundaries between the various phases (i.e., foam, microsphere, opaque solution, and precipitate) may be ascertained. Appropriate ranges of hydrophilicity and average degree of polymerization for the formation of microspheres may then be determined.

The term "pharmacologically acceptable" is used herein in the conventional sense and indicates that the selected gas is biocompatible and has minimal toxicity.

The term "water-insoluble gas" as used herein relates to gases with relatively low solubility in water (i.e., in the aqueous phase of the microsphere suspension), preferably with a Bunsen Coefficient of less than 0.01 mL gas per mL of solution at 25° C. The Bunsen Coefficient characterizes the solubility of a gas in a solvent, and reflects the volume of gas which is absorbed by a unit volume of solvent at a specified temperature and pressure. See, for example, Wen, W. -Y., Muccitelli, J. A., *J. Sol. Chem.*, 1979, Vol. 8, pp. 225–240.

Examples of pharmacologically acceptable water-insoluble gases include fluorine-containing gases such as sulfur hexafluoride, and perhalogenated alkanes having from 1 to 5 carbon atoms, more preferably 3 to 5 carbon atoms. Examples of $C_1$–$C_5$ perhalogenated alkanes include perfluoroalkanes, such as perfluoromethane (i.e., $CF_4$), perfluoroethane (i.e., $CF_3CF_3$), perfluoropropane (i.e., $CF_3CF_2F_3$), perfluoro-n-butane (i.e., $CF_3CF_2CF_2CF_3$), perfluoro-isobutane $(CF_3CF(CF_3)_2)$, perfluoro-n-pentane (i.e., $CF_3CF_2CF_2CF_2CF_3$), perfluoro-isopentane $(CF_3CF_2CF(CF_3)_2)$, and perfluoro-neopentane (i.e., $C(CF_3)_4$), and mixed perhalogenated alkanes, such as 1-chloroheptafluoropropane (i.e., $ClCF_2CF_2CF_3$) and 1-bromoheptafluoropropane (i.e., $BrCF_2CF_2CF_3$). The perfluorinated $C_1$–$C_5$ alkanes are gases at physiological temperature (i.e., 37° C.) and pressure (i.e., 1 atm). Table 1 gives the Bunsen Coefficients of several gases.

TABLE 1

BUNSEN COEFFICIENTS OF GASES IN WATER
(1 atmosphere, mL/mL)

| Gas | 5° C. | 25° C. |
| --- | --- | --- |
| Carbon Dioxide | 1.383 | 0.824 |
| Argon | 0.047 | 0.033 |
| Oxygen | 0.043 | 0.031 |
| Nitrogen | 0.021 | 0.016 |
| Sulfur hexafluoride | 0.008 | 0.0054 |
| Perfluoromethane | 0.0082 | 0.00504 |
| Perfluoroethane | 0.0027 | 0.00138 |
| Perfluoropropane | 0.0016 | not available |
| Perfluorobutane | 0.0007 | not available |

The sizes and distribution of sizes of the gas-filled microspheres of the present invention may be determined using any of a variety of well-known methods, including, for example, a suitable particle counter such as a Coulter Multisizer II (Coulter Electronics, Hialeah, Fla.). The gas-filled microsphere size distribution may be altered by fractionation into larger or smaller microsphere populations.

The gas-filled microspheres of the present invention are of a size suitable for transpulmonary passage, with a mean diameter less than 10 microns and greater than 0.1 microns. The maximum size (mean diameter) of the microsphere is defined by that size which will pass through the pulmonary capillaries. In the case of humans, that size will typically be less than about 10 microns. Correspondingly, the minimum size is that which will provide efficient acoustic scattering at the ultrasonic frequencies typically used for ultrasonic imaging. (The frequency may vary with the mode of imaging, e.g., transthoracic, transesophageal, and will normally be in the range of 2–12 MHz.) The minimum size will typically be about 0.1 microns. The typical mean size of the microspheres used in the invention method will be about 2 to about 7 micrometers. This size will permit their passage through capillaries, if necessary, without being filtered out prior to reaching the area to be imaged (e.g., where a peripheral venous injection site is used). Thus, microspheres within the present invention will be capable of perfusing tissue and producing an enhanced image of the tissue, organs and any differentiation between well-perfused and poorly-perfused tissue, without being injected into the arteries or directly into the area to be imaged. Accordingly, they may be injected into a peripheral vein or other predetermined area of the body, resulting in considerably less invasion than the arterial injections required for an angiogram.

The gas-filled microspheres of the present invention are echo reflective (i.e., capable of reflecting ultrasound waves) since they are composed of materials having acoustic properties which are significantly different from those of blood or tissue. The microspheres of the present invention may be used for imaging a wide variety of areas. These areas include, but are not limited to, myocardial tissue, liver, spleen, kidney, and other tissues and organs presently imaged by ultrasonic techniques.

The microspheres may or may not be concentrated by removal of excess aqueous phase, or collected and resuspended in a second aqueous solution. Suspensions of microspheres are made by diluting the microspheres after formation to a desired concentration of preferably about $5\times10^7$ to about $5\times10^9$ microspheres per mL of suspending liquid which can be any aqueous, biologically-compatible liquid. Examples of such liquids are buffers, saline, protein solutions and sugar solutions.

A microsphere suspension within the present invention is stable both in vivo and in vitro. Stability in vivo is a function of the ability of a concentrated suspension (approximately $1\times10^9$ microspheres per mL) to withstand 40 pounds per square inch (psi) pressure as evidenced by no appreciable change in size distribution after one minute at this pressure.

In terms of method of operation, the use of the subject microspheres would be the same as that of conventional ultrasonic contrast agents. The amount of microspheres used would be dependent on a number of factors including the choice of liquid carriers (water, sugar solution, etc.), degree of opacity desired, areas of the body to be imaged, site of injection and number of injections. In all instances, however, sufficient microspheres would be used in the liquid carrier to achieve enhancement of discernable images by the use of ultrasonic scanning.

All publications and patent applications cited in this specification are herein incorporated by reference as if each individual publication or patent application were specifically and individually indicated to be incorporated by reference.

The present invention is further illustrated by the following examples. These examples are not intended to limit the invention in any manner.

EXAMPLE 1

Preparation of Block Co-polymer PSLGlu-block-PLLeu

Gamma-methyl-L-glutamate N-carboxy anhydride ("MLGlu-NCA") was prepared from gamma-methyl-L-glutamic acid ("MLGlu"; the gamma —COOH group protected as the ester —COOCH$_3$) and phosgene (COCl$_2$) in tetrahydrofuran (THF) using the phosgene method. MLGlu-NCA (MW 187, 1.496 g, 8.0 mmol) was suspended in 10 mL of anhydrous ethylene dichloride ("EDC", ClCH$_2$CH$_2$Cl). N,N-dimethylethylenediamine ("N,N-DMEDA," 13.6 mg, 154 micromol) was added with vigorous stirring. As carbon dioxide (CO$_2$) evolved, the MLGlu-NCA went slowly into solution and after 2 hours of mixing, a clear solution of poly(methyl-L-glutamate (i.e., "PMLGlu") has formed.

L-Leucine-N-carboxy anhydride ("LLeu-NCA", MW 157, 0.314 g, 2 mmol) was dissolved in 1 mL of EDC, and was added to the PMLGlu solution. The reaction was continued for another 4 hours with the evolution of more CO$_2$, after which a clear and viscous solution of the block co-polymer, PMLGlu-block-PLLeu, was obtained.

The co-polymer was subsequently hydrolyzed (deprotected) to convert the methyl ester of the glutamate groups to sodium form to yield the PSLGlu-block-PLLeu block co-polymer. Methanol (CH$_3$OH, 10 mL) and n-propanol (CH$_3$CH$_2$CH$_2$OH, 10 mL) were added to the block co-polymer solution. A sodium hydroxide solution (NaOH, 10% by weight, 8 mL) was subsequently slowly added, and the mixture stirred at room temperature for 10 hours. As the reaction proceeded, the co-polymer precipitated. After the hydrolysis was complete, the supernatant was decanted, and the precipitate washed with methanol (CH$_3$OH) in vacuo. The block co-polymer PSLGlu-block-PLLeu was obtained as a white water soluble powder (yield 1.8 g). The average degree of polymerization, DPn, was calculated to be approximately (8 mmol+2 mmol)/154 micromol=65. The hydrophilicity was calculated to be approximately (8 mmol)/(8 mmol+2 mmol)=0.80.

EXAMPLE 2

Preparation of Microspheres by a Batch Process

Figure 2:
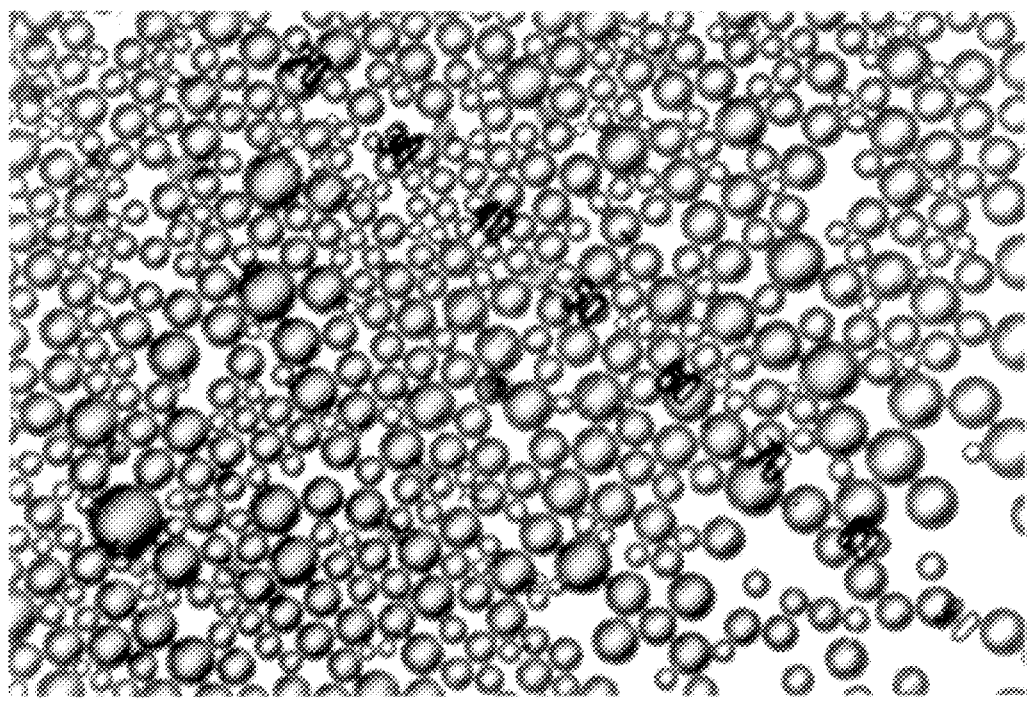
FIG. 2 is a photograph of the gas filled microspheres prepared by sonication of the block co-polymer PSLGlu-block-PLLeu in the presence of perfluoropropane (1 unit= 1.5 micron).

The block co-polymer PMLGlu-PLLeu obtained in Example 1 (100 mg) was dissolved in 10 mL of a 0.2M sodium acetate buffer (pH 6.5), that is, to give a 1.0% solution. The solution was sonicated using a 0.5 inch horn, 1500 watts, 20 kilohertz, at 60% output for 8 seconds, while perfluoropropane gas was bubbled through the solution. A photograph of the resulting gas-filled microspheres is shown in FIG. 1. The size distribution of the gas-filled microspheres was evaluated with the aid of a Coulter Multisizer II; the results are shown in FIG. 2. A mean microsphere size of 2.92 micrometer was determined, with a concentration of $9.17 \times 10^8$ microspheres/ml, yielding a calculated combined microsphere volume of 0.012 cm$^3$ of encapsulated gas per ml of suspension.

Figure 3:
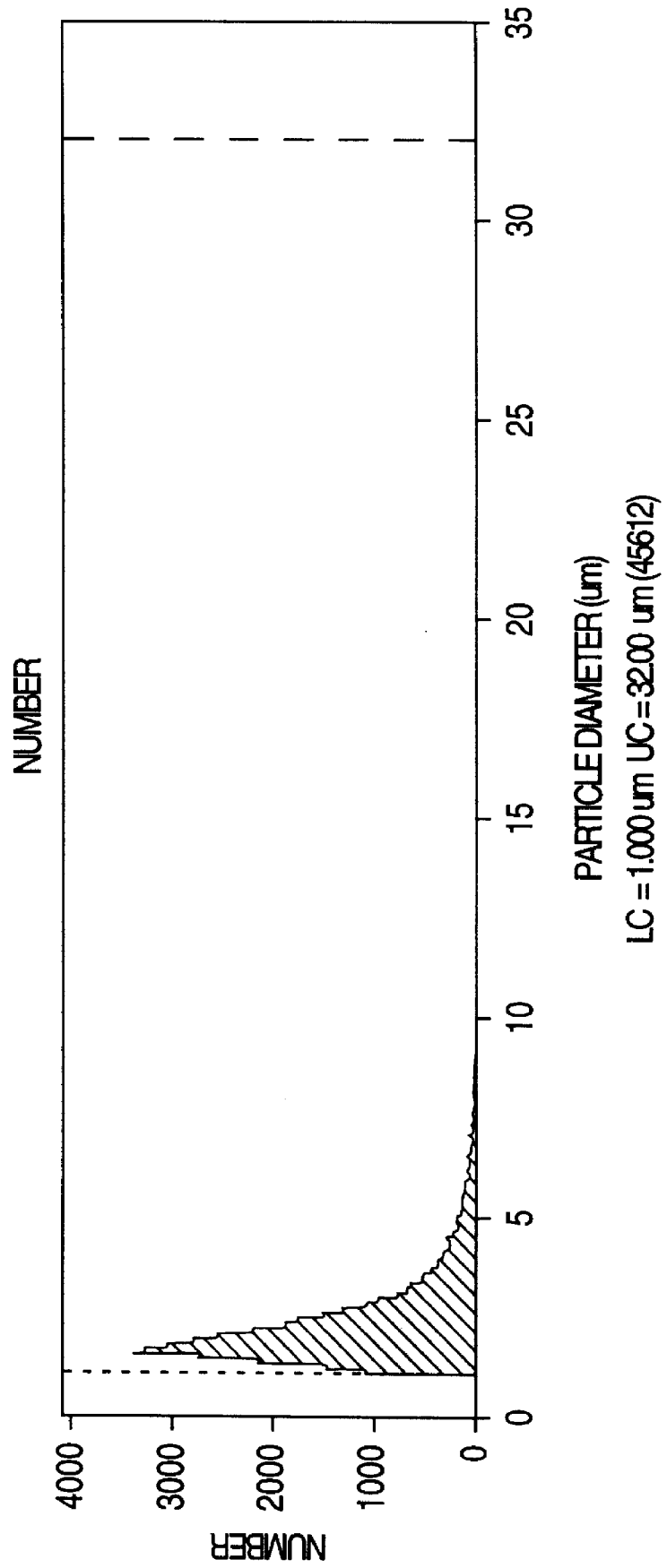
FIG. 3 is a graph depicting the microsphere population as a function of microsphere diameter as determined using a Coulter counter for microspheres prepared using the block co-polymer PSLGlu-block-PLLeu and perfluoropropane.
Figure 4:
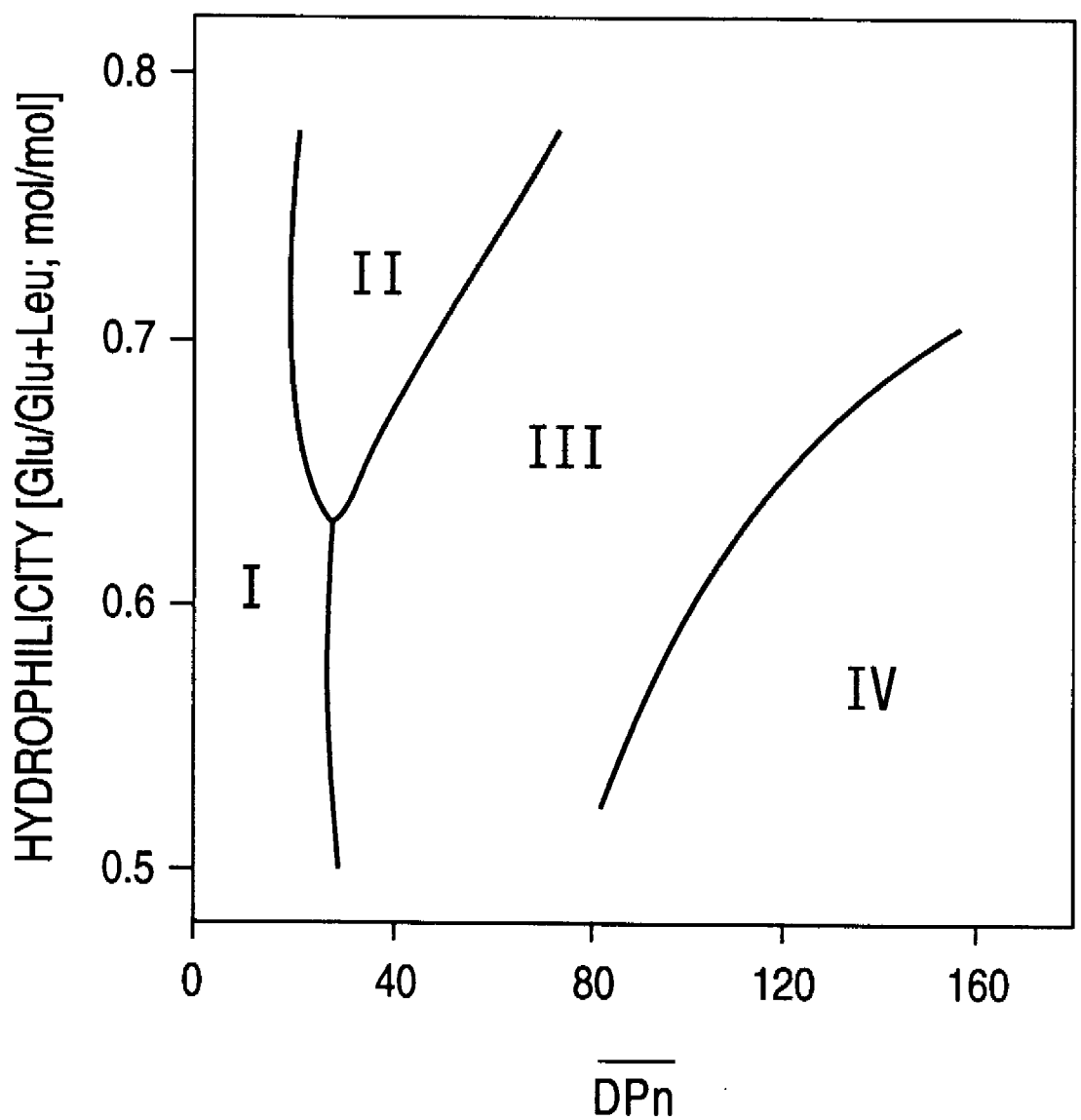
FIG. 4 is a phase diagram of the PSLGlu-block-PLLeu block co-polymer gas-filled microspheres. Phases are denoted (I) foam, (II) microsphere, (III) opaque solution, and (IV) precipitate.

In FIG. 3 is shown a phase diagram for PSLGlu-block-PLLeu block co-polymers. The calculated average degree of polymerization appears along the horizontal axis with values from 0 to about 160, and the calculated hydrophilicity (i.e., Glu/(Glu+Leu) in this case) appears along the vertical axis with values from about 0.5 to about 0.9. About two dozen different PSLGlu-block-PLLeu block co-polymers were prepared and subjected to cavitation so as to determine the approximate boundaries of the (I) foam, (II) microsphere, (III) opaque solution, and (IV) precipitate phases, as shown in the figure. Hydrophilicities of about 0.65 to about 0.90 and average degrees of polymerization of about 30 to about 100 were found to favor microsphere formation. Thus a block co-polymer with a hydrophilicity of about 0.75 and a degree of polymerization of about 40, which corresponds to a $(Glu)_{30}(Leu)_{10}$ block co-polymer, would be predicted to yield microspheres.

EXAMPLE 3
Preparation of Microspheres by a Continuous Process

Figure 5:
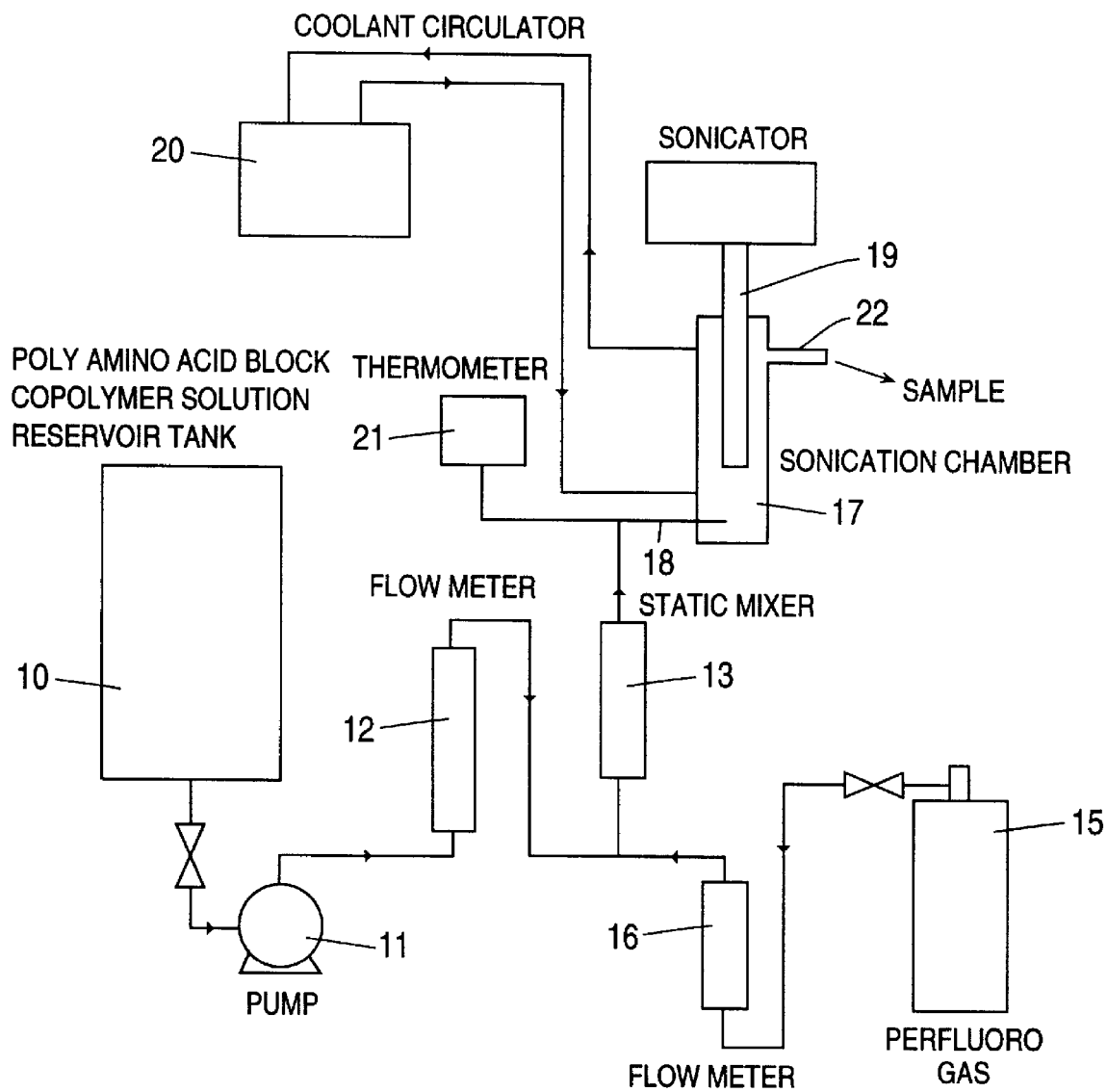
FIG. 5 is a schematic representation of an apparatus suitable for continuous process sonication to form microspheres.

The gas-filled microspheres of the present invention may also be prepared using a continuous process. An apparatus suitable for such a continuous process is shown schematically in FIG. 5.

A solution of the block co-polymer PSLGlu-block-PLLeu in an aqueous buffer of 0.1M sodium bicarbonate (pH 8.0) was provided in a reservoir tank (10), and introduced into a static mixer (13), with the aid of a pump (11) and a flowmeter (12) at a rate of 20 mL/min. A water-insoluble gas was provided in a reservoir tank (15), and introduced into the static mixer (13) via a flowmeter (16) at a rate of 8 mL/min. The polymer-gas mixture was introduced from the static mixer (13) into a sonication chamber (17, 40 mL capacity) via an inlet (18), in which was submersed a 0.5 inch horn, 1500 watt, 20 kilohertz sonication horn (19), which was operated at 60% output. The sonication chamber (17) was maintained at 30° C. using a coolant circulator (20). The temperature of the polymer-gas mixture was monitored using a thermometer (21). The sonicated polymer-gas mixture, containing microspheres, was removed from the sonication chamber (17) via an outlet (22).

EXAMPLE 4
In Vivo Ultrasound Using Block Co-polymer Microspheres as an US Contrast Agent Microspheres prepared as described in Examples 2 or 3 are used in diagnostic imaging as follows: For a dog weighing approximately 25 kg, a 1.0 mL volume of a microsphere suspension containing from about $5 \times 10^7$ to about $5 \times 10^9$ microspheres per mL is injected into a peripheral (cephalic) vein at a rate of 0.3 mL per second. Images of the heart are acquired using a Hewlett Packard Sonos 1500 (Andover, Mass.) ultrasonograph in the B-mode using a transthoracic 5.0 mHz transducer. Images are recorded at a frame rate of 30 frames per second throughout the procedure and stored on S-VHS tape for later processing.

What is claimed is:

1. A composition for use as an ultrasonic imaging agent comprising a suspension of gas-filled microspheres, said microspheres comprising:

a) an outer membrane comprising an amphiphilic amino acid block copolymer, said copolymer consisting of a hydrophobic polymer block of hydrophobic amino acids, and a hydrophilic polymer block of hydrophilic amino acids; and b) a pharmacologically acceptable water-insoluble gas encapsulated by said outer membrane.

2. The composition of claim 1, wherein said hydrophobic amino acids are alpha-amino acids.

3. The composition of claim 1, wherein said hydrophobic amino acids are alpha-amino acids selected from the group consisting of leucine, isoleucine, valine, and phenylalanine.

4. The composition of claim 1, wherein said hydrophobic amino acids are leucine.

5. The composition of claim 1, wherein said hydrophilic amino acids are alpha-amino acids.

6. The composition of claim 1, wherein said hydrophilic amino acids are alpha-amino acids selected from the group consisting of glutamic acid, glutamate, aspartic acid, aspartate, and lysine.

7. The composition of claim 1, wherein said hydrophilic alpha amino acids are glutamate.

8. The composition of claim 1, wherein said water-insoluble gas is a perfluoroalkane having 1 to 5 carbon atoms.

9. The composition of claim 1, wherein said water-insoluble gas is a perfluoroalkane having 3 to 5 carbon atoms.

10. The composition of claim 1, wherein said water-insoluble gas is perfluoropropane.

11. The composition of claim 1, wherein said hydrophobic amino acids are alpha-amino acids selected from the group consisting of leucine, isoleucine, valine, and phenylalanine; said hydrophilic amino acids are alpha-amino acids selected from the group consisting of glutamic acid, glutamate, aspartic acid, aspartate, and lysine; and said water-insoluble gas is a perfluoroalkane having 1 to 5 carbon atoms.

12. The composition of claim 11, wherein said hydrophobic amino acids are leucine; said hydrophilic amino acids are glutamate; and said water-insoluble gas is perfluoropropane.

13. The composition of claim 1, wherein said co-polymer is PSLGlu-block-PLLeu.

14. The composition of claim 13, wherein said co-polymer is PSLGlu-block-PLLeu, and said co-polymer has a DPn of about 65 and a hydrophilicity of about 0.8.

15. The composition of claim 11, wherein said water-insoluble gas is perfluoropropane.

16. A method of enhancing the contrast of tissues and/or organs of a patient in an ultrasonic image thereof, comprising the steps:

(a) injecting the composition of claim 1 into the patient;

(b) applying ultrasonic energy to said tissue and/or organs;

(c) detecting ultrasonic energy that is reflected from the tissues and/or organs; and (d) translating the reflected energy into an image.

* * * * *